(12) United States Patent
de la Vega Sanchez de Lozada

(10) Patent No.: US 11,533,972 B2
(45) Date of Patent: Dec. 27, 2022

(54) ANTI-BACTERIAL AND DEODORIZING ATHLETIC BAG

(71) Applicant: Rafael de la Vega Sanchez de Lozada, Colorado Springs, CO (US)

(72) Inventor: Rafael de la Vega Sanchez de Lozada, Colorado Springs, CO (US)

(73) Assignee: Salt Athletic, Inc., Colorado Springs, CO (US)

( * ) Notice: Subject to any disclaimer, the term of this patent is extended or adjusted under 35 U.S.C. 154(b) by 327 days.

(21) Appl. No.: 16/745,014

(22) Filed: Jan. 16, 2020

(65) Prior Publication Data

US 2020/0221836 A1 Jul. 16, 2020

Related U.S. Application Data

(60) Provisional application No. 62/793,271, filed on Jan. 16, 2019.

(51) Int. Cl.
| | | |
|---|---|---|
| *A45C 3/12* | (2006.01) | |
| *A01N 59/20* | (2006.01) | |
| *A45C 13/02* | (2006.01) | |
| *A61L 2/238* | (2006.01) | |
| *A61L 9/014* | (2006.01) | |

(52) U.S. Cl.
CPC .............. *A45C 3/12* (2013.01); *A01N 59/20* (2013.01); *A45C 13/02* (2013.01); *A61L 2/238* (2013.01); *A61L 9/014* (2013.01); *A45C 2013/026* (2013.01)

(58) Field of Classification Search
CPC ..... A45C 3/12; A45C 13/02; A45C 2013/026; A01N 59/20; A61L 2/238; A61L 9/014
See application file for complete search history.

(56) References Cited

U.S. PATENT DOCUMENTS

| | | | |
|---|---|---|---|
| 5,427,453 A | 6/1995 | Cloessner | |
| 6,467,613 B2 | 10/2002 | Felsenthal | |
| 7,260,853 B2 | 8/2007 | Newman | |
| 7,621,430 B2 * | 11/2009 | Schawbel | A47G 25/60 |
| | | | 223/86 |
| 8,192,537 B2 | 6/2012 | Alemao | |

(Continued)

FOREIGN PATENT DOCUMENTS

| | | |
|---|---|---|
| CN | 203342078 U | 5/2013 |
| KR | 20060080693 A | 1/2006 |

(Continued)

OTHER PUBLICATIONS

PCT Search Report from corresponding PCT Application No. PCT/US2020/013926, dated Apr. 21, 2020.

(Continued)

*Primary Examiner* — Tri M Mai

(74) *Attorney, Agent, or Firm* — Holzer Patel Drennan

(57) ABSTRACT

Athletic footwear often emits unpleasant odors after being used. As a result, athletic footwear is sometimes placed in a separate shoe bag with the purpose of carrying the footwear in isolation. However, current bags for athletic footwear have little to no effect on absorbing or neutralizing unpleasant odors, they merely contain the odor. The presently disclosed technology provides a space effective, odor-combatting athletic shoe bag.

18 Claims, 6 Drawing Sheets

(56) References Cited

U.S. PATENT DOCUMENTS

| | | | |
|---|---|---|---|
| 8,387,783 B2 * | 3/2013 | Zack | A47K 3/001 206/77.1 |
| 8,726,534 B2 | 5/2014 | Chappell et al. | |
| 9,399,834 B1 * | 7/2016 | Drake | A61L 2/202 |
| 9,554,601 B2 * | 1/2017 | Arajakis | A45F 4/12 |
| 9,849,055 B2 | 12/2017 | Vertsteylen et al. | |
| 2003/0156767 A1 | 8/2003 | Valdez | |
| 2004/0173056 A1 | 9/2004 | McNally et al. | |
| 2005/0028909 A1 * | 2/2005 | Matlhako | A45C 13/08 150/103 |
| 2008/0235985 A1 * | 10/2008 | Gordon | A43B 7/12 206/278 |
| 2012/0128271 A1 * | 5/2012 | Dias | A45C 3/001 112/475.08 |
| 2013/0318922 A1 * | 12/2013 | Lloyd | A61M 16/0672 383/105 |
| 2014/0186224 A1 | 7/2014 | Derby Krans | |
| 2014/0352859 A1 | 12/2014 | Brown | |
| 2015/0129629 A1 | 5/2015 | Voggenthaler et al. | |
| 2016/0317405 A1 | 11/2016 | Brain et al. | |
| 2017/0022640 A1 | 1/2017 | Schenk et al. | |
| 2018/0116311 A1 | 5/2018 | Callison | |
| 2018/0229914 A1 * | 8/2018 | Bahrami | B01D 53/0407 |
| 2020/0121025 A1 * | 4/2020 | Wiegele | A43B 7/00 |

FOREIGN PATENT DOCUMENTS

| | | | |
|---|---|---|---|
| WO | 0115747 A1 | 3/2001 | |
| WO | 2017083738 A2 | 5/2017 | |

OTHER PUBLICATIONS

PCT Written Opinion from corresponding PCT Application No. PCT/US2020/013926, dated Apr. 21, 2020.

New Odor-Eliminating Shoe Bag Aercase Stepping Out for Funding on Kickstarter. Aercase. PRWeb.com. EVO. Sep. 27, 2016. p. 2 [Retrieved on Nov. 12, 2018]. Retrieved from the Internet: <URL: https://www.prweb.com/releases/2016/09/prweb13716438.htm>.

SmellRid Reusable Charcoal Shoe Odor Eliminator Pouches. SmellRid. SmellRid. Nov. 8, 2018. pp. 1-2 [Retrieved on Nov. 12, 2018]. Retrieved from the Internet: <URL: https://smellrid.com/smellrid-reusable-charcoal-shoe-odor-eliminator-pouches.html>.

* cited by examiner

ANTI-BACTERIAL AND DEODORIZING ATHLETIC BAG

CROSS-REFERENCE TO RELATED APPLICATIONS

The present application claims benefit of priority to U.S. Provisional Patent Application No. 62/793,271 entitled "Anti-Bacterial and Deodorizing Athletic Bag" and filed on Jan. 16, 2019, which is specifically incorporated by reference herein for all that it discloses or teaches.

BACKGROUND

Athletic footwear often emits unpleasant odors after being used, often due to moisture and bacteria buildup therein, which is at least in part caused by the sweat of an athlete's feet during athletic activity. This moisture buildup is typically slow to dissipate over time. As a result, athletic footwear is sometimes placed in a separate shoe bag with the purpose of carrying the footwear in isolation. However, current bags for athletic footwear have little to no effect on absorbing or neutralizing unpleasant odors, they merely contain the odor. Further, current bags for athletic footwear are often bulky and wasteful of space.

SUMMARY

The presently disclosed technology provides a space effective, odor-combatting athletic shoe bag. The bag may contain a divider in the middle where shoes are placed tip-first and corresponding soles face the divider. The bag may be narrow at a bottom closed end and increasing in width toward a top openable end to accommodate the shape of typical athletic footwear.

BRIEF DESCRIPTIONS OF THE DRAWINGS

DETAILED DESCRIPTIONS

Figure 1:
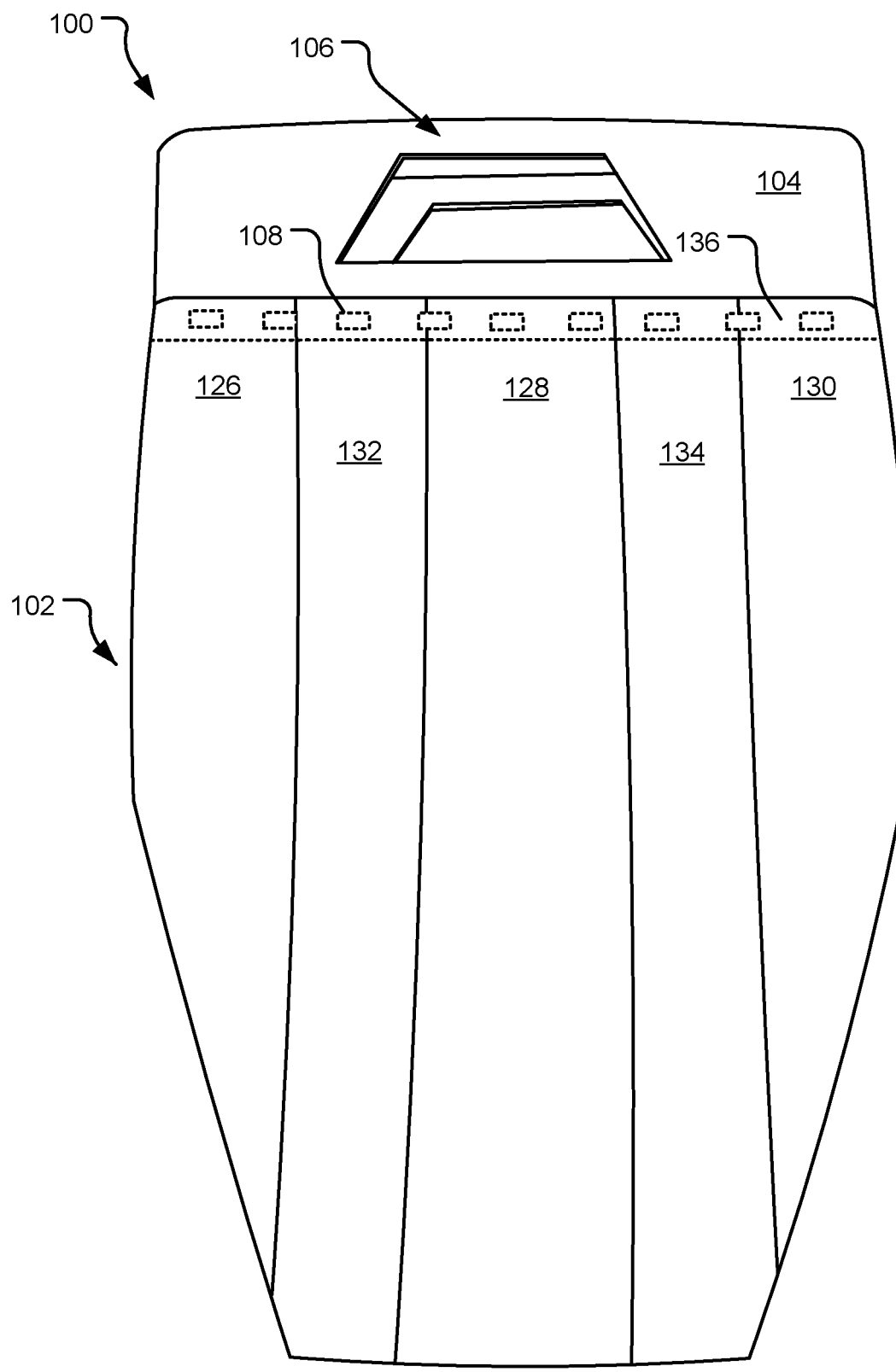
FIG. 1 illustrates a front perspective view of an example anti-bacterial and deodorizing athletic bag in a closed orientation.

FIG. 1 illustrates a front perspective view of an example anti-bacterial and deodorizing athletic bag 100 in a closed orientation. The bag 100 includes a main body 102 that is sized and shaped to encompass a pair of shoes (not shown, see e.g., shoes 418, 420 of FIG. 4) in a specific orientation, an internal divider (not shown, see e.g., divider 210 of FIG. 2), and a closure assembly 104 at a selective opening (not shown, see e.g., opening 212 of FIG. 2). The main body 102 forms a cavity therein for storing shoes with the selective opening for placing (or receiving) and removing the shoes.

Various panels of the main body 102 may be made of one or more of the following material layers. An outermost exterior-facing layer in panels 126, 128, 130 of the main body 102 is made of a low-permeability fabric (e.g., a ripstop nylon, in some cases including a non-permeable coating such as silicone). The low-permeability fabric layer is designed to be moisture and air impervious, or of limited porosity, to seal odors within the bag 100. The low-permeability fabric layer is also durable, with tear and abrasion resistance as it is the outermost layer and may be exposed to the elements. In other panels 132, 134 of the main body 102, the exterior-facing low-permeability fabric layer is omitted. In other implementations, a different count and/or location of panels of the main body 102 includes exterior-facing low-permeability fabric, as well as a different count and/or location of panels of the main body 102 that omits the exterior-facing low-permeability fabric.

An innermost (or interior) layer, at least in some panels of the main body 102 is made of a high-permeability fabric (e.g., spandex or another readily pervious and breathable fabric) layer, that may also be significantly elastic. The elasticity of the high-permeability fabric layer may help to adapt the main body 102 to fit a variety of shoe sizes and shapes. Further, in various implementations, the high-permeability fabric layer may be infused with a biocidal metal (e.g., biocidal metal plated or incorporating biocidal metal threads). The high-permeability fabric layer permits moisture to flow therethrough while presenting a smooth appearance to a user and smooth surface to interface with the shoes stored within the bag 100. In some regions of the main body 102, the high-permeability fabric layer may be omitted.

Activated charcoal (or carbon) is a material that has been treated with oxygen to become porous and to have an extraordinarily large surface area. This makes it very effective in containing and treating unpleasant odors. Various metals (e.g., silver, gold, copper, nickel, tin, and zinc) have an oligodynamic effect (also referred to herein as a biocidal effect), which renders them effective at odor control by killing bacteria within the bag 100. Such metals are referred to herein as biocidal metals. Biocidal metal may be generally applied to textiles as further odor control agent. In specific regions of the main body 102, odor-absorbing panels of one or both of activated carbon cloth and a biocidal metal plated nylon knit mesh is added either between the low-permeability fabric layer and the high-permeability fabric layer, or in some implementations used for panels of the main body 102 in place of one or both of the low-permeability fabric layer and the high-permeability fabric layer. The activated carbon cloth is adept at absorbing moisture within the bag 100 and neutralizing odors associated with the moisture. In some implementations, the odor-absorbing panels may also be infused with essential oils or other scented materials to mask any remaining odor.

The closure assembly 104 selectively seals the bag 100 and includes a carrying handle 106 and a series of magnets (e.g., magnet 108) arranged in a row on each side of the selective opening in the bag 100. In other implementations, the closure assembly 104 includes s singular elongated magnet on each side of a selective opening in the bag 100. Each of these types of closure assembly 104 may be referred to herein as a magnetic zipper. The magnets, as well as a flap 136 securing the magnets, is illustrated in broken lines as they are hidden from view in the front perspective view of the bag 100 of FIG. 1. An opening in each side of the closure assembly 104 forms the carrying handle 106. The carrying handle 106 is separated by pulling the magnets apart to open the bag 100 and brought together to meet and close the bag 100 and allow the magnets to secure together. In other implementations, the closure assembly 104 includes a drawstring or zippered opening in place of the depicted magnetic zipper.

The closure assembly 104 provides an affirmative and tight seal, though not necessarily airtight or watertight. In other implementations, the closure assembly 104 may include a zipper, hook-and-loop fasteners, or other mechanism(s) for selectively holding the handle 106 together. Other closure mechanisms are also contemplated herein. Further, separate carrying handles may be attached to or otherwise incorporated into the bag 100 in lieu of or in addition to the carrying handle 106.

In some implementations, the bag 100 also includes a rigid or semi-rigid framework that holds the bag 100 in a desired shape and holds the main body 102 open to selectively place and remove athletic equipment from the bag 100. Still further, the rigid or semi-rigid framework may merely be applied to one or more compartments within the bag 100 to hold the compartment(s) open to selectively place and remove athletic equipment from the bag 100. Still further, the compartments may each include one or more anti-bacterial and deodorizing panels, such as odor-absorbing panel 546 of FIG. 5, that face particular pieces of athletic equipment. The compartments may be located within the bag 100, or attached to exterior surfaces of the bag 100, or some combination thereof. In an example implementation, a pair of soccer cleats is stored within a compartment or compartments within the bag 100 having anti-bacterial and deodorizing panels, and a pair of soccer shin guards are stored within a compartment or compartments attached to the exterior of the bag 100, also having anti-bacterial and deodorizing panels.

Various pieces of athletic equipment that may be stored in anti-bacterial and deodorizing compartments within the bag 100 include, but are not limited to shoes, helmets, body pads, and other athletic clothing. The athletic equipment may be that common to sports such as soccer, rugby, hockey, lacrosse, basketball, football, tennis, running, and so on. The bag 100 may be specifically adapted to apply to gear for a particular sport. In various implementations, a rear-side of the bag 100 is similar to the front-side of the bag 100 depicted in FIG. 1 and described in detail above.

Figure 2:
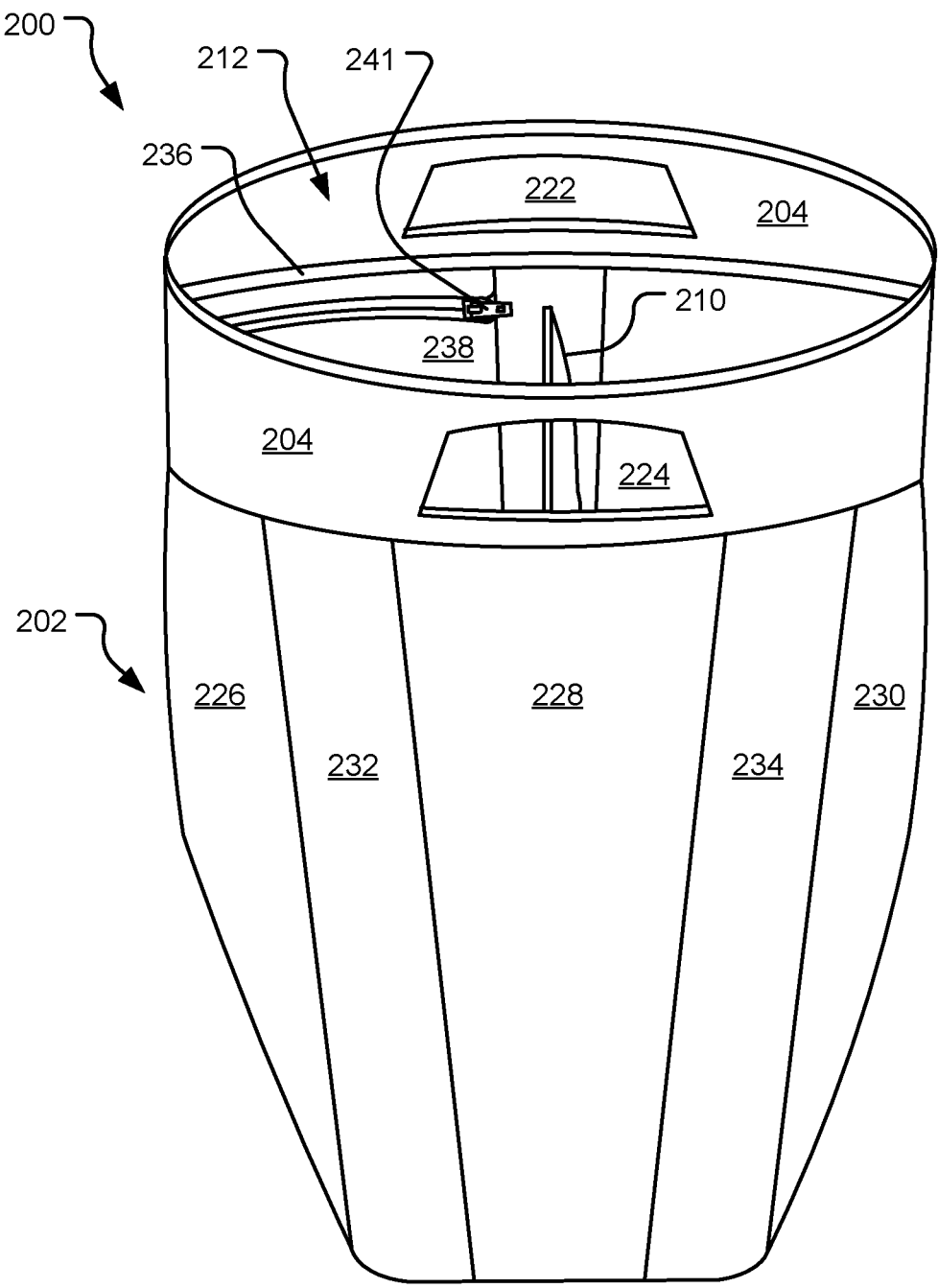
FIG. 2 illustrates a front perspective view of an example anti-bacterial and deodorizing athletic bag in an open orientation.

FIG. 2 illustrates a front perspective view of an example anti-bacterial and deodorizing athletic bag 200 in an open orientation. The bag 200 includes a main body 202 that is sized and shaped to encompass a pair of shoes (not shown, see e.g., shoes 418, 420 of FIG. 4) in a specific orientation, an internal divider 210, and a closure assembly 204 at a selective opening 212. The main body 202 forms a cavity therein for storing shoes with the selective opening for placing and removing the shoes.

Various panels of the main body 202 may be made of one or more of the following material layers. An outermost exterior-facing layer in panels 226, 228, 230 of the main body 202 is made of a low-permeability fabric layer. In other panels 232, 234 of the main body 202, the exterior-facing low-permeability fabric layer is omitted. In other implementations, a different count and/or location of panels of the main body 202 includes the exterior-facing low-permeability fabric, as well as a different count and/or location of panels of the main body 202 that omits the exterior-facing low-permeability fabric. An innermost layer, at least in some panels of the main body 202 is made of a high-permeability fabric that may also be significantly elastic. In some regions of the main body 202, the high-permeability fabric layer may be omitted. In specific regions of the main body 202, odor-absorbing panels of one or both of activated carbon cloth and a biocidal metal plated nylon knit mesh is added either between the low-permeability fabric layer and the high-permeability fabric layer, or in some implementations used for panels of the main body 202 in place of one or both of the low-permeability fabric layer and the high-permeability fabric layer.

The closure assembly 204 selectively seals the bag 200 and includes a carrying handle and a series of magnets (not shown, see e.g., magnet 108 of FIG. 1) arranged in a row on each side of the selective opening 212 in the bag 200 with flap 236 securing the magnets in place. Openings 222, 224 in opposing sides of the closure assembly 204 forms a carrying handle for the bag 200. The carrying handle is separated by pulling the magnets apart to open the bag 200 and brought together to meet and close the bag 200 and allow the magnets to secure together.

The bag 200 further includes an internal pocket 238 that provides additional compartmentalized storage within the bag 200. The internal pocket 238 may be selectively opened and closed using a zipper 241 or other selective closure (e.g., a hook-and-loop fastener, button(s), a magnetic closure, etc.). In various implementations, a rear-side of the bag 200 is similar to the front-side of the bag 200 depicted in FIG. 2 and described in detail above.

Figure 3:
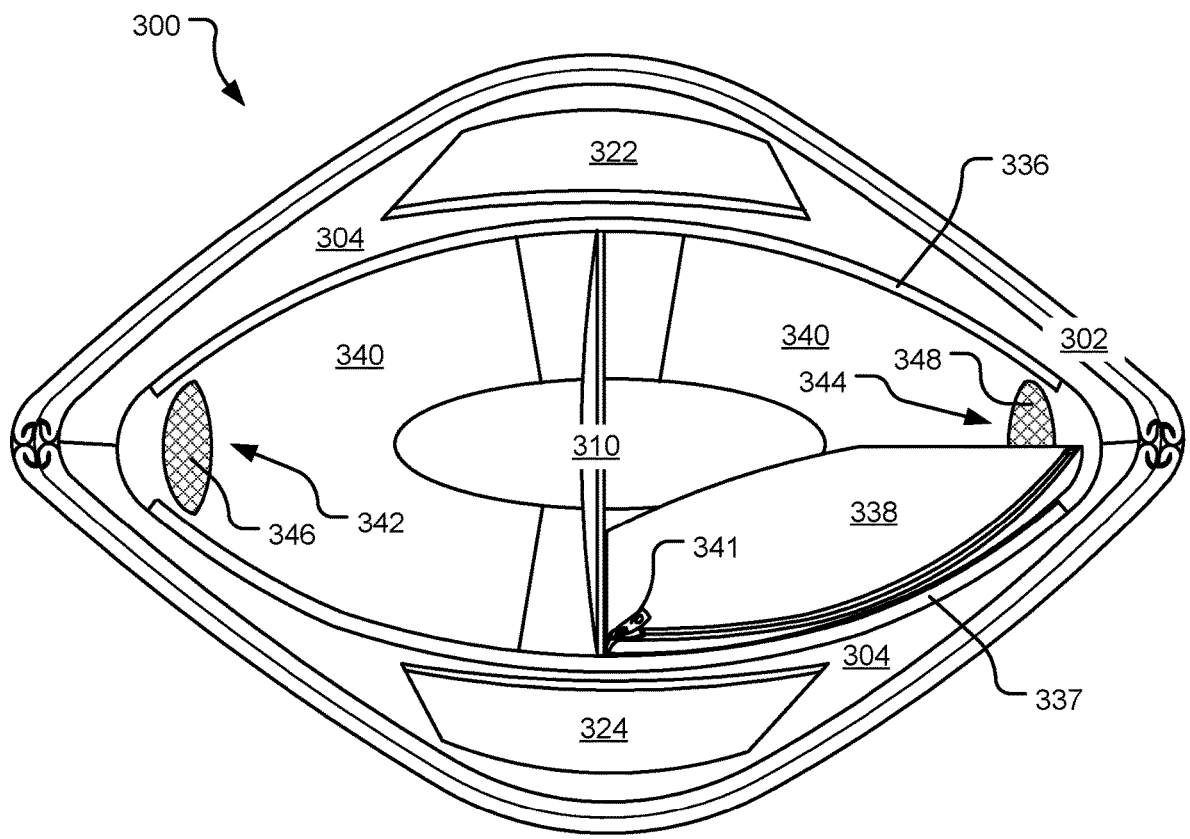
FIG. 3 illustrates an interior view of an example anti-bacterial and deodorizing athletic bag in an open orientation.

FIG. 3 illustrates an interior view of an example anti-bacterial and deodorizing athletic bag 300 in an open orientation. The bag 300 includes a main body 302 that is sized and shaped to encompass a pair of shoes (not shown, see e.g., shoes 418, 420 of FIG. 4) in a specific orientation, an internal divider 310, and a closure assembly 304 at a selective opening. The main body 302 forms a cavity therein for storing shoes with the selective opening for placing and removing the shoes.

Various panels of the main body 302 may be made of one or more of the following material layers. An outermost exterior-facing layer in some panels of the main body 302 is made of a low-permeability fabric. In other panels of the main body 302, the exterior-facing low-permeability fabric layer may be omitted. An innermost layer 340, at least in some panels of the main body 302 is made of a high-permeability fabric that may also be significantly elastic. In some regions of the main body 302, the high-permeability fabric layer may be omitted. In specific regions of the main body 302, odor-absorbing panels 346, 348 of one or both of activated carbon cloth and a biocidal metal plated nylon knit mesh is added either between the low-permeability fabric layer and the high-permeability fabric layer, or in some implementations used for panels of the main body 302 in place of one or both of the low-permeability fabric layer and the high-permeability fabric layer. Specific locations of the odor-absorbing panels 346, 348 within the main body 302, as well as number, size, and shape of the odor-absorbing panels 346, 348 may vary from that shown in FIG. 3 and explicitly described.

The innermost layer 340 includes windows 342, 344 in the high-permeability fabric layer, each of which provide an opening to the odor-absorbing panels 346, 348 of activated carbon cloth and/or biocidal metal plated nylon knit mesh. In some implementations, the windows 342, 344 include a mesh that permits the odor-absorbing panels 346, 348 to be visible through the windows 342, 344, while still adequately containing the odor-absorbing panels 346, 348 generally behind the innermost layer 340 of high-permeability fabric. In various implementations, the windows 342, 344 are specifically oriented within the interior of the main body 302 to face an opening of one of the pair of shoes. As a result, the portion of a shoe that typically emits the greatest amount of moisture and odor (i.e., the foot opening) directly faces the windows 342, 344 and the odor-absorbing panels 346, 348 therein. In other implementations, the windows 342, 344 may be omitted.

The closure assembly 304 selectively seals the bag 300 and includes a carrying handle and a series of magnets (not shown, see e.g., magnet 108 of FIG. 1) arranged in a row on each side of the selective opening in the bag 300 with flaps 336, 337 securing the magnets in place. Openings 322, 324 in opposing sides of the closure assembly forms a carrying handle for the bag 300. The carrying handle is separated by pulling the magnets apart to open the bag 300 and brought together to meet and close the bag 300 and allow the magnets to secure together. The bag 300 further includes an internal pocket 338 that provides additional compartmentalized storage within the bag 300. The internal pocket 338 may be selectively opened and closed using a zipper 341 or other selective closure.

Figure 4:
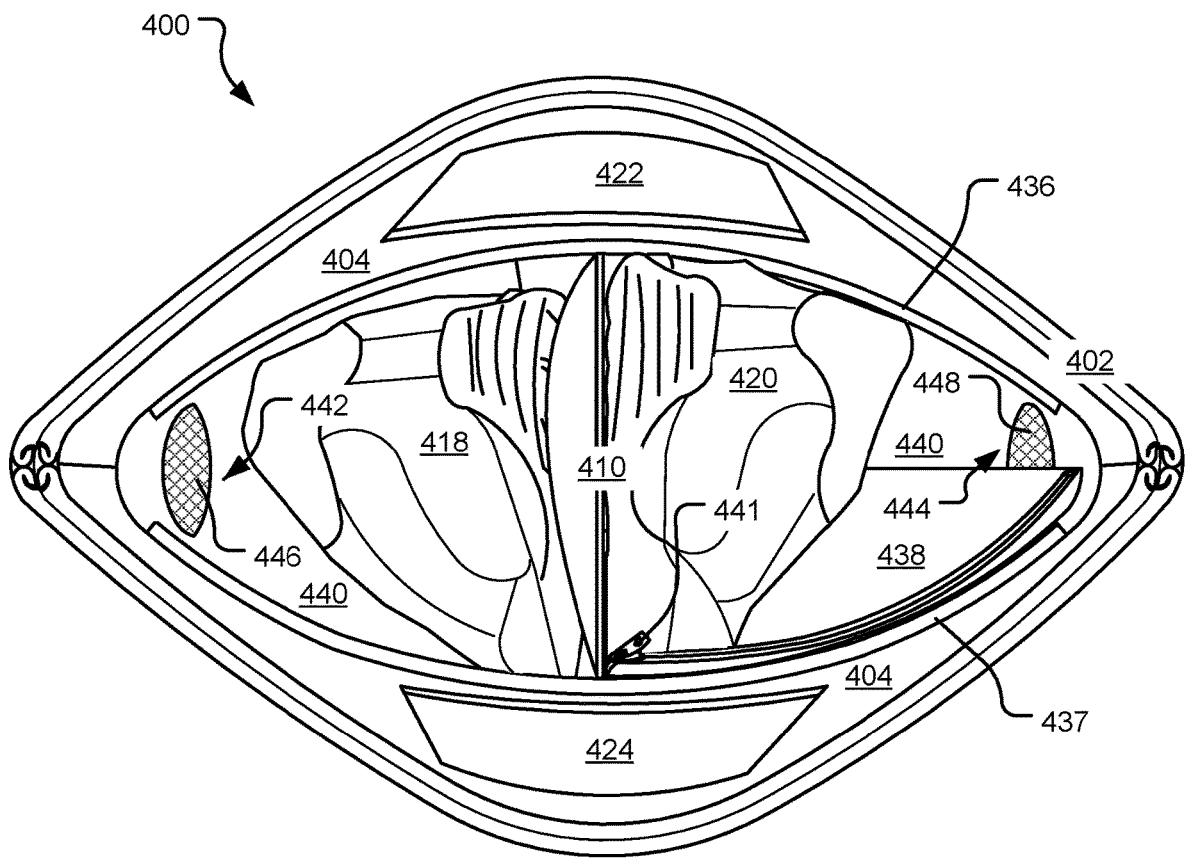
FIG. 4 illustrates an interior view of an example anti-bacterial and deodorizing athletic bag in an open orientation with a pair of athletic shoes positioned therein.

FIG. 4 illustrates an interior view of an example anti-bacterial and deodorizing athletic bag 400 in an open orientation with a pair of athletic shoes 418, 420 positioned therein. The bag 400 includes a main body 402 that is sized and shaped to encompass the shoes 418, 420 in the depicted orientation, an internal divider 410, and a closure assembly 404 at a selective opening. The main body 402 forms a cavity therein for storing the shoes 418, 420 with the selective opening for placing and removing the shoes 418, 420. The internal divider 410 physically separates the shoes 418, 420, or in other implementations, two or more components of other athletic equipment.

Various panels of the main body 402 may be made of one or more of the following material layers. An outermost exterior-facing layer in some panels of the main body 402 is made of a low-permeability fabric. In other panels of the main body 402, the exterior-facing low-permeability fabric layer may be omitted. An innermost layer 440, at least in some panels of the main body 402 is made of a high-permeability fabric that may also be significantly elastic. In some regions of the main body 402, the high-permeability fabric layer may be omitted. In specific regions of the main body 402, odor-absorbing panels 446, 448 of one or both of activated carbon cloth and a biocidal metal plated nylon knit mesh is added either between the low-permeability fabric layer and the high-permeability fabric layer, or in some implementations used for panels of the main body 402 in place of one or both of the low-permeability fabric layer and the high-permeability fabric layer. Specific locations of the odor-absorbing panels 446, 448 within the main body 402, as well as number, size, and shape of the odor-absorbing panels 446, 448 may vary from that shown in FIG. 4 and explicitly described.

The innermost layer 440 includes windows 442, 444 in the high-permeability fabric material, each of which provide an opening to the odor-absorbing panels 446, 448 of activated carbon cloth and/or biocidal metal plated nylon knit mesh. In some implementations, the windows 442, 444 include a mesh that permits the odor-absorbing panels 446, 448 to be visible through the windows 442, 444, while still adequately containing the odor-absorbing panels 446, 448 generally behind the innermost layer 440 of low-permeability fabric material. In various implementations, the windows 442, 444 are specifically oriented within the interior of the main body 402 to each face an opening of one of the shoes 418, 420. As a result, the portion of a shoe that typically emits the greatest amount of moisture and odor (i.e., the foot opening) directly faces the windows 442, 444 and the odor-absorbing panels 446, 448 therein. In other implementations, the windows 442, 444 may be omitted.

The closure assembly 404 selectively seals the bag 400 and includes a carrying handle and a series of magnets (not shown, see e.g., magnet 108 of FIG. 1) arranged in a row on each side of the selective opening in the bag 400 with flaps 436, 437 securing the magnets in place. Openings 422, 424 in opposing sides of the closure assembly forms a carrying handle for the bag 400. The carrying handle is separated by pulling the magnets apart to open the bag 400 and brought together to meet and close the bag 400 and allow the magnets to secure together. The bag 400 further includes an internal pocket 438 that provides additional compartmentalized storage within the bag 400. The internal pocket 438 may be selectively opened and closed using a zipper 441 or other selective closure.

Figure 5:
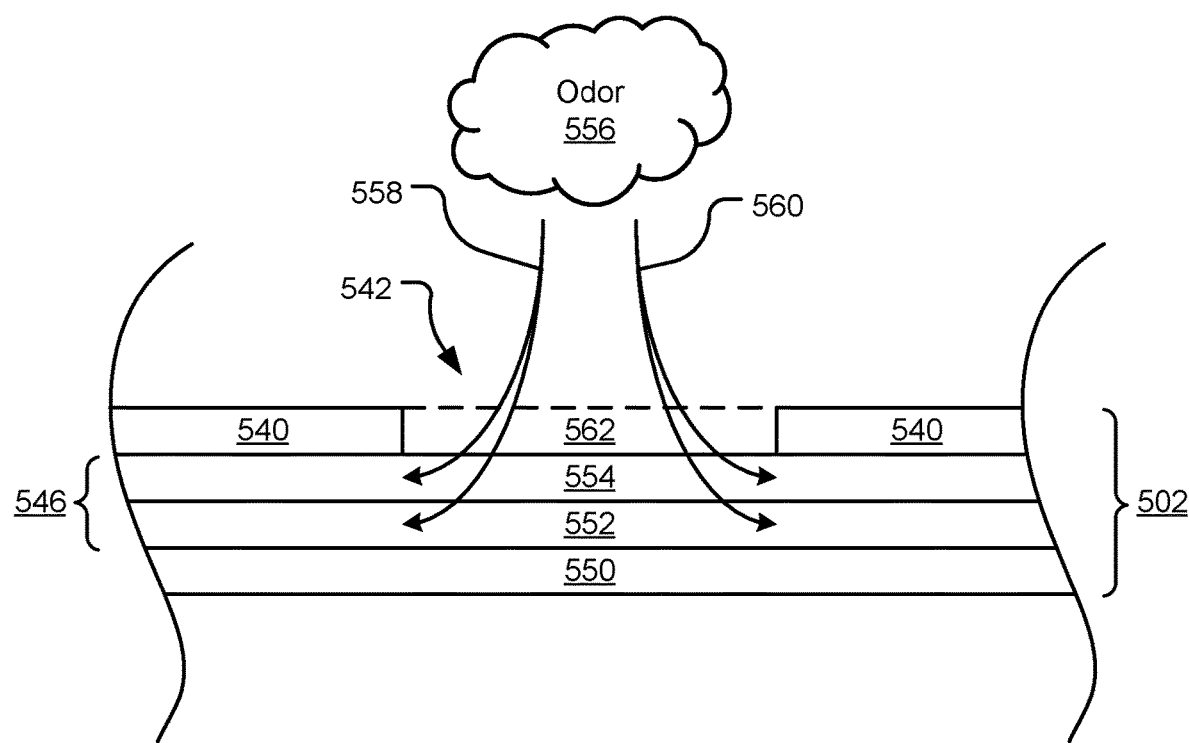
FIG. 5 illustrates a diagrammatic sectional view of a main body of an example anti-bacterial and deodorizing athletic bag.

FIG. 5 illustrates a diagrammatic sectional view of a main body 502 of an example anti-bacterial and deodorizing athletic bag. An outermost exterior-facing layer 550 of the main body 502 is made of a low-permeability fabric (e.g., a ripstop nylon). Low-permeability fabric within the meaning of the present application may include fabrics with greater than 17 Ret under the ISO 11092 standard (also referred to as the sweating guarded hotplate (SGHP) test). In other panels of the main body 502, the exterior-facing low-permeability fabric layer 550 may be omitted.

An innermost layer 540 of the main body 502 is made of a high-permeability fabric (e.g., spandex or another readily pervious and breathable fabric) that may also be significantly elastic. High-permeability fabric within the meaning of the present application may include fabrics with less than 17 Ret under the ISO 11092 standard. In some regions of the main body 502, the high-permeability fabric layer 540 may be omitted.

In specific regions of the main body 502, odor-absorbing panels (e.g., odor-absorbing panel 546) of one or both of activated carbon cloth 552 and a biocidal metal plated nylon knit mesh 554 is added either between the low-permeability fabric layer 550 and the high-permeability fabric layer 540, or in some implementations used for panels of the main body 502 in place of one or both of the low-permeability fabric layer 550 and the high-permeability fabric layer 540.

The activated carbon cloth 552 is adept at absorbing moisture within the bag and neutralizing odor 556 associated with moisture therein. The biocidal metal plated nylon knit mesh 554 has anti-microbial properties, which may further aid in neutralizing the odor 556 by killing bacteria within the bag. In one example implementation, the odor-absorbing panel 546 is approximately 5 inches square (i.e., 5 inches square+/−1 square inch). Specific locations of the odor-absorbing panel 546 (or other similar odor-absorbing panels) within the main body 502, as well as number, size, and shape of the odor-absorbing panels may vary from that explicitly described.

The innermost layer 540 includes a window 542 in the high-permeability fabric layer 540 that provides an opening to the odor-absorbing panel 546 of activated carbon cloth 552 and biocidal metal plated nylon knit mesh 554, thereby facilitating absorption of the odor 556, as illustrated by arrows 558, 560. In some implementations, the window 542 includes a mesh 562 that permits the odor-absorbing panel 546 to be visible through the window 542, while still adequately containing the odor-absorbing panel 546 generally behind the innermost layer of high-permeability fabric 540 within the main body 502.

In various implementations, the window 542 is specifically oriented within the main body 502 to face an opening of one of a pair of shoes. As a result, the portion of a shoe that typically emits the greatest amount of moisture and odor (i.e., the foot opening) directly faces the window 542 and the odor-absorbing panel 546 therein. In other implementations, the window 542 may be omitted and the odor 556 permeates the high-permeability fabric layer 540 prior to being absorbed/dissipated by the odor-absorbing panel 546.

In another implementation, the odor-absorbing panel 546 is only attached to the low-permeability fabric layer 550 at one end. The opposite end of the odor-absorbing panel 546 is free, thus forming an insert. Further, the odor-absorbing panel 546 may be reconfigured as a bag or pocket made of biocidal metal plated nylon knit mesh and filled at least in part with activated carbon material. The bags or pockets may also be filled with additional resiliently compressible material (e.g., foam) to provide an expandable characteristic to fill a desired void.

In a specific example, the bags or pockets are shoe inserts and are sized and shaped to be stuffed into shoe openings of shoes stored within the bag. The shoe inserts are then capable of partially or completely filling the void within each shoe and more directly interact with odor-causing moisture and bacteria to eliminate or block the odor 556. In another implementation, the shoe inserts include a rigid or semi-rigid structure with a shape conforming to the interior of the shoes (e.g., a shoe last). The structure is coated or covered with activated carbon cloth and/or biocidal metal plated nylon knit mesh, or the structure is perforated and the activated carbon cloth and/or biocidal metal plated nylon knit mesh is contained within the structure, or some combination thereof.

Figure 6:
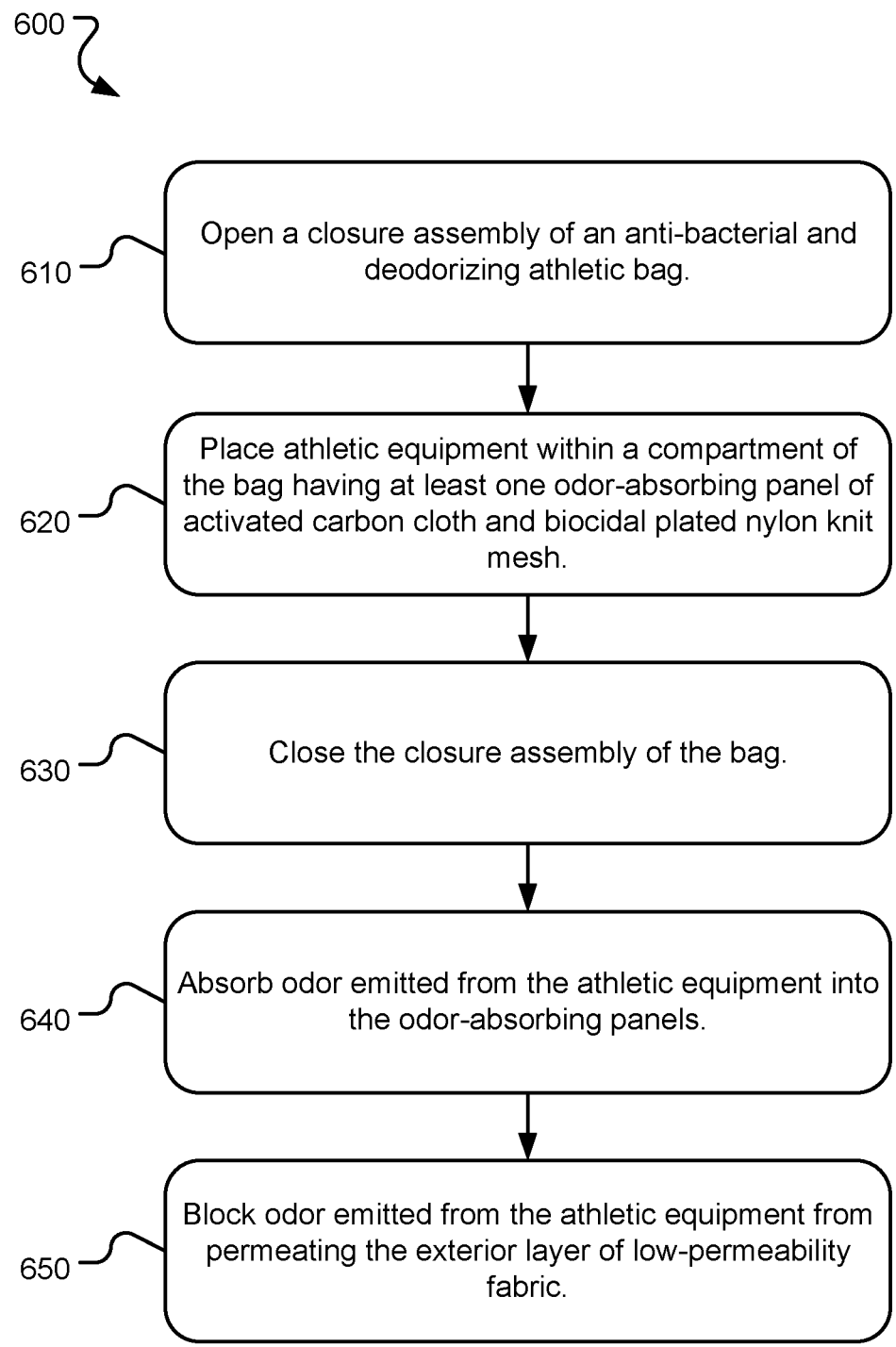
FIG. 6 illustrates example operations for using an anti-bacterial and deodorizing athletic bag.

FIG. 6 illustrates example operations 600 for using an anti-bacterial and deodorizing athletic bag. An opening operation 610 opens a closure assembly of the bag, exposing at least one compartment therein that is used to store athletic equipment. The compartment includes at least one odor-absorbing panel attached to an interior of the main body that includes at least one layer of each of activated carbon cloth and biocidal metal plated nylon knit mesh. In various implementations, the closure assembly may include one or more zippers, drawstrings, buttons, snaps, handles, magnets, and so on.

A placing operation 620 places the athletic equipment into the compartment with the odor-absorbing panels each facing a portion of the athletic equipment generating odor. In an implementation where the athletic equipment is a pair of shoes, the odor-absorbing panels each face an opening in each shoe for the user's foot. A closing operation 630 closes the closure assembly of the bag, thus sealing the athletic equipment within the bag. While the closure assembly generally seals the bag, in various implementations it may not be air-tight or watertight. Such shoe bags may have a single compartment or one or more internal dividers of pockets separating the bag into multiple compartments. Further, such shoe bags may have a variety of closure structures, including but not limited to draw strings, buckles, zippers, buttons, and the like.

An absorbing operation 640 absorbs odor emitted from the athletic equipment into the odor-absorbing panels. One or both of the activated carbon cloth and biocidal metal plated nylon knit mesh within the odor-absorbing panel primarily performs the absorbing operation 640. A blocking operation 650 blocks odor emitted from the athletic equipment from permeating the exterior layer of low-permeability fabric. As the exterior layer of low-permeability fabric has low or no permeability, odors generated by the athletic equipment are trapped within the bag while being absorbed by the odor-absorbing panels.

The logical operations making up the embodiments of the invention described herein are referred to variously as operations, steps, objects, or modules. Furthermore, it should be understood that logical operations may be performed in any order, adding or omitting operations as desired, unless explicitly claimed otherwise or a specific order is inherently necessitated by the claim language.

The above specification, examples, and data provide a complete description of the structure and use of exemplary embodiments of the invention. Since many embodiments of the invention can be made without departing from the spirit and scope of the invention, the invention resides in the claims hereinafter appended. Furthermore, structural features of the different embodiments may be combined in yet another embodiment without departing from the recited claims.

What is claimed is:

1. An anti-bacterial and deodorizing athletic bag comprising:
    a main body of a size and shape to encompass athletic equipment generating odor, the main body including an opening for receiving the athletic equipment into the athletic bag, and the main body further including at least an exterior layer of low-permeability fabric and an interior layer of high-permeability fabric; and
    one or more odor-absorbing panels attached to an interior of the main body, the odor-absorbing panels including at least one layer of each of an activated carbon cloth and a biocidal metal plated nylon knit mesh, the odor-absorbing panels each facing a portion of the athletic equipment generating odor, wherein each of the odor-absorbing panels lie within a window in the interior layer of high-permeability fabric.

2. The anti-bacterial and deodorizing athletic bag of claim 1, wherein the low-permeability fabric is made of a ripstop nylon and the high-permeability fabric is made of spandex.

3. The anti-bacterial and deodorizing athletic bag of claim 1, wherein the biocidal metal plated nylon knit mesh includes one or more of silver, gold, copper, nickel, tin, and zinc.

4. The anti-bacterial and deodorizing athletic bag of claim 1, wherein athletic equipment is a pair of shoes, and the odor-absorbing panels each face an opening of one of the shoes.

5. The anti-bacterial and deodorizing athletic bag of claim 1, wherein the windows in the interior layer of high-permeability fabric are covered by a mesh, and wherein the odor-absorbing panels are visible through the mesh.

6. The anti-bacterial and deodorizing athletic bag of claim 1, further comprising:
    an internal divider physically separating two or more components of the athletic equipment.

7. The anti-bacterial and deodorizing athletic bag of claim 1, wherein the interior layer of high-permeability fabric is elastic to accommodate a variety of sizes and shapes of the athletic equipment.

8. The anti-bacterial and deodorizing athletic bag of claim 1, wherein the interior layer of high-permeability fabric is infused with a biocidal metal.

9. The anti-bacterial and deodorizing athletic bag of claim 1, wherein the odor-absorbing panels are further infused with a scented material.

10. The anti-bacterial and deodorizing athletic bag of claim 1, further comprising:
a closure assembly for the athletic bag including a magnetic zipper and a pair of handles that meet and secure together for a user to carry the athletic bag.

11. The anti-bacterial and deodorizing athletic bag of claim 1, further comprising:
an internal pocket formed from a layer of the high-permeability fabric.

12. A method of using an anti-bacterial and deodorizing athletic bag comprising:
opening a closure mechanism of the bag, the bag including a main body of a size and shape to encompass athletic equipment generating odor, the main body including at least an exterior layer of low-permeability fabric and an interior layer of high-permeability fabric;
placing the athletic equipment into a compartment of the bag, the compartment including at least one odor-absorbing panel incorporating at least one layer of each of activated carbon cloth and biocidal metal plated nylon knit mesh, the odor-absorbing panels each facing a portion of the athletic equipment generating odor, and wherein each of the odor-absorbing panels lie within a window in the interior layer of high-permeability fabric; and
closing the closure mechanism of the bag, thus sealing the athletic equipment within the bag.

13. The method of claim 12, further comprising:
absorbing odor emitted from the athletic equipment into the odor-absorbing panels.

14. The method of claim 12, further comprising:
blocking odor emitted from the athletic equipment from permeating the exterior layer of low-permeability fabric.

15. The method of claim 12, wherein the low-permeability fabric is made of a ripstop nylon and the high-permeability fabric is made of spandex.

16. The method of claim 12, wherein the biocidal metal plated nylon knit mesh includes one or more of silver, gold, copper, nickel, tin, and zinc.

17. The method of claim 12, wherein athletic equipment is a pair of shoes, and the odor-absorbing panels each face an opening of one of the shoes.

18. An anti-bacterial and deodorizing athletic shoe bag comprising:
a main body of a size and shape to encompass athletic shoes generating odor, the main body including an opening for receiving the athletic shoes into the athletic shoe bag, and the main body further including at least an exterior layer of low-permeability fabric and an interior layer of high-permeability fabric; and
one or more odor-absorbing panels attached to an interior of the main body, the odor-absorbing panels including at least one layer of each of an activated carbon cloth and a biocidal metal plated nylon knit mesh, the odor-absorbing panels each facing an opening on one of the athletic shoes generating odor, wherein each of the odor-absorbing panels lie within a window in the interior layer of high-permeability fabric.

* * * * *